US005827702A

United States Patent [19]
Cuthbertson

[11] Patent Number: 5,827,702
[45] Date of Patent: Oct. 27, 1998

[54] OCULAR GENE THERAPY

[75] Inventor: R. Andrew Cuthbertson, San Francisco, Calif.

[73] Assignee: Genentech, Inc., So. San Francisco, Calif.

[21] Appl. No.: 332,566

[22] Filed: Oct. 31, 1994

[51] Int. Cl.$^6$ .......................... C12N 15/00; A61K 48/00
[52] U.S. Cl. ................................. 435/172.1; 435/172.3; 435/320.1; 514/44; 935/55; 935/56; 935/57
[58] Field of Search ................... 514/44, 2; 435/320.1, 435/172.3, 172.1, 172.2, 240.1; 424/93.1, 93.2, 93.21; 935/55, 56, 57

[56] References Cited

FOREIGN PATENT DOCUMENTS 9401139  1/1994  WIPO .

OTHER PUBLICATIONS

Bennett, J., et al., "Photoreceptor cell rescue in retinal degeneration (rd) mice by in vivo gene therapy", *Nature Medicine*, 2(6):649–654 (1996).
Roth, J.A., et al., "Retrovirus–mediated wild–type p53 gene transfer to tumors of patients with lung cancer", *Nature Medicine*, 2(9):985–991 (1996).
Marshall, E. "Gene Therapy's Growing Pains", *Science* 269: 1050–1055 (1995).
Jomary, C. et al. "Adenovirus–mediated gene transfer to murine retinal cells in vitro and in vivo", *FEBS Letters* 347: 117–122 (1994).
Thompson, H. W. et al. "High levels of in vivo gene transfer to corneal epithelium and endothelium", Invest. Opthal, Vis. Sci. 4: 1383 (1994).
Miller et al., FASEB J., 9:190–199, 1995.
Culver et al., Trends in Genetics, 10(5): 174–178, 1994.
Hodgson, Exp. Opin. Ther. Pat., 5(5):459–468, 1995.
Bennett, Jean, et al., "Adenovirus Vector–Mediated In Vivo Gene Transfer Into Adult Murine Retina", *Investigative Ophthalmology & Visual Science*, 35(5):2535–2542 (1994).
Zack, Donald J., "Ocular Gene Therapy", *Arch Ophthalmology*, 111:1477–1479 (1993).
Travis, G. H., et al., "Complete Rescue of Photoreceptor Dysplasia and Degeneration in Transgenic retinal degeneration slow (rds) Mice", *Neutron*, 9:113–119 (1992).
Li, T, et al., "In Vivo Transfer of a Reporter Gene to the Retina Mediated by an Adenoviral Vector", *Investigative Ophthalmology & Visual Science*, 335(5):2543–2547 (1994).
Bok, Dean, "Retinal Transplantation and Gene Therapy", *Investigative Ophthalmology & Visual Sciences*, 34(3) "473–476 (1993).
"Control of Gene Expression, Gene Transfer and Differential Display in the Eye–Poster Presentation, Sarasota Visual Art Center", *Investigative Ophthalmology & Visual Sciences*, 35(4):1705 (1994).
Lem, Janis et al., "Retinal degeneration is rescued in transgenic rd mice by expression of the cGMP phosphodiesterase β subunit," *Proc. Natl. Acad. Sci. USA*, 89:4422–4426 (1992).
Nih "Report and Recommendations . . . ", Orkin et al. Dec. 7, 1995, 1–40.
LaFont et al., Lancet 346:1442–1443, 1995.

*Primary Examiner*—Bruce R. Campell
*Attorney, Agent, or Firm*—Flehr Hohbach Test Albritton & Herbert LLP; Walter H. Dreger; Robin M. Silva

[57] ABSTRACT

The invention relates to methods of ocular gene therapy.

5 Claims, 2 Drawing Sheets

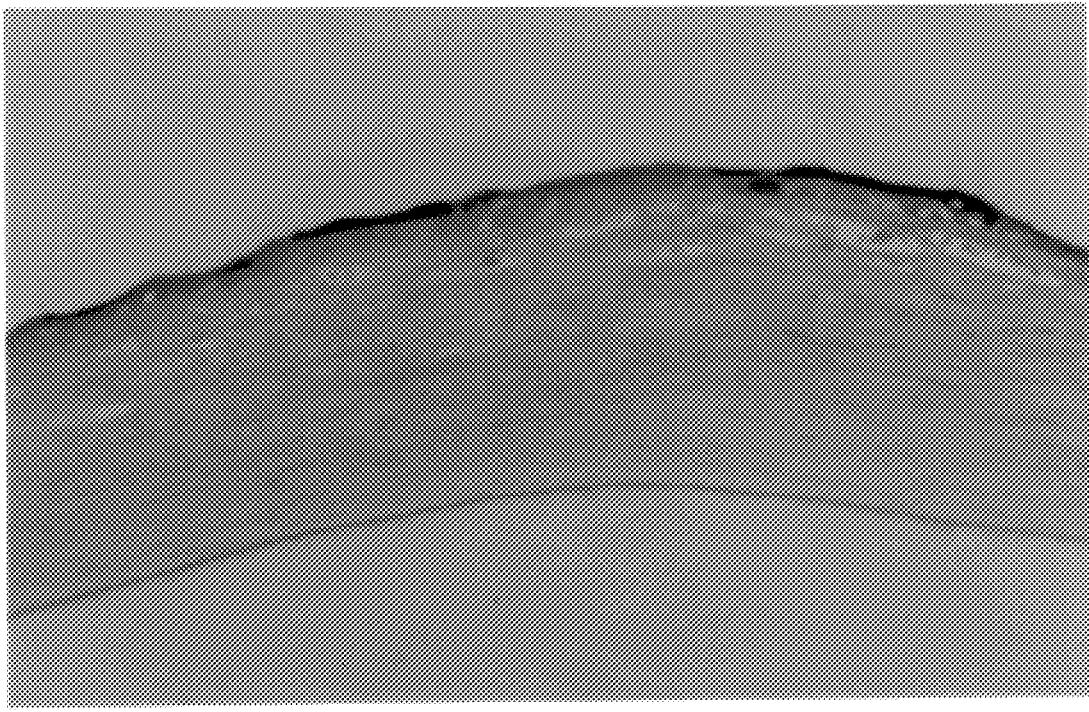
FIG._1A
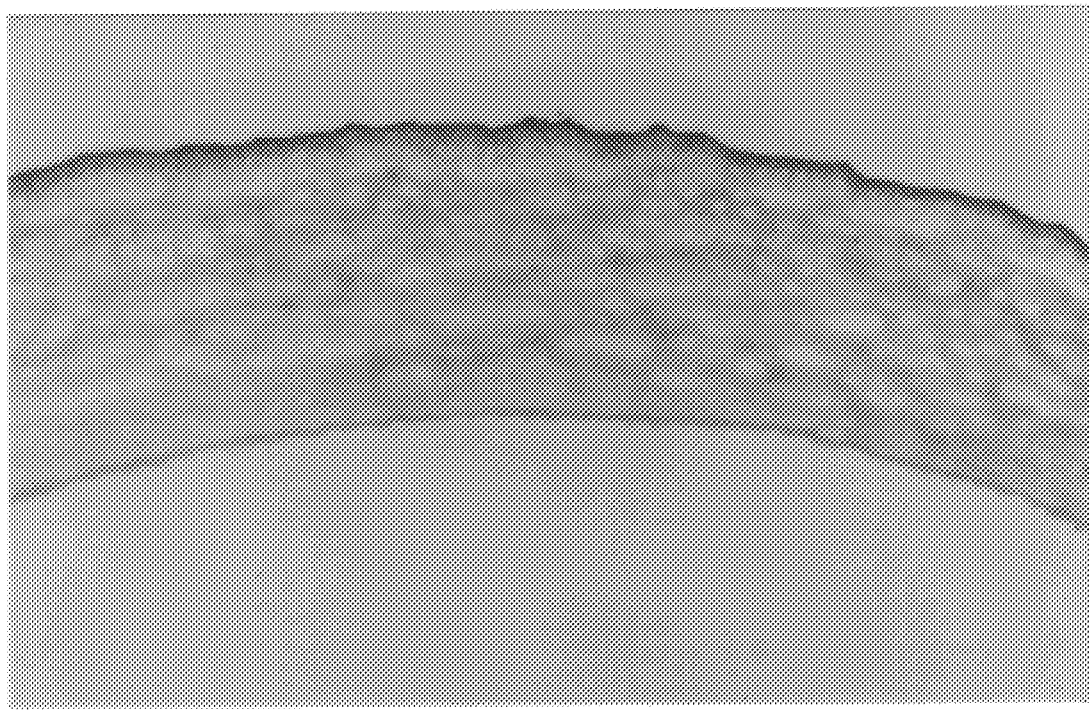
FIG._1B

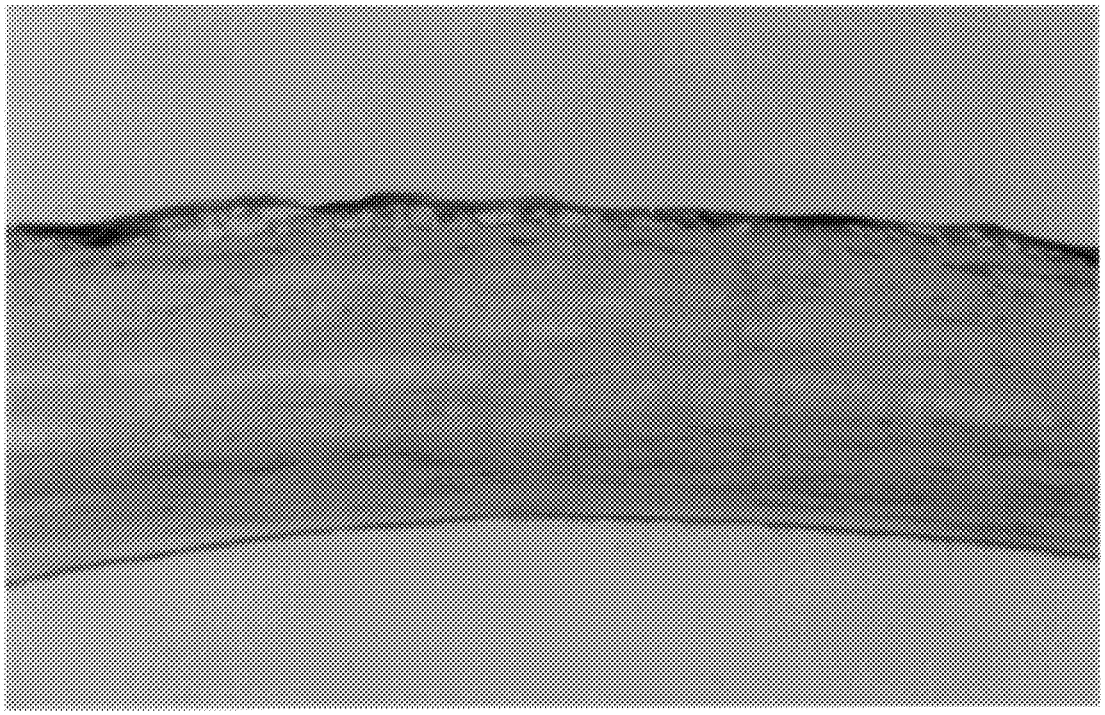
*FIG._2A*
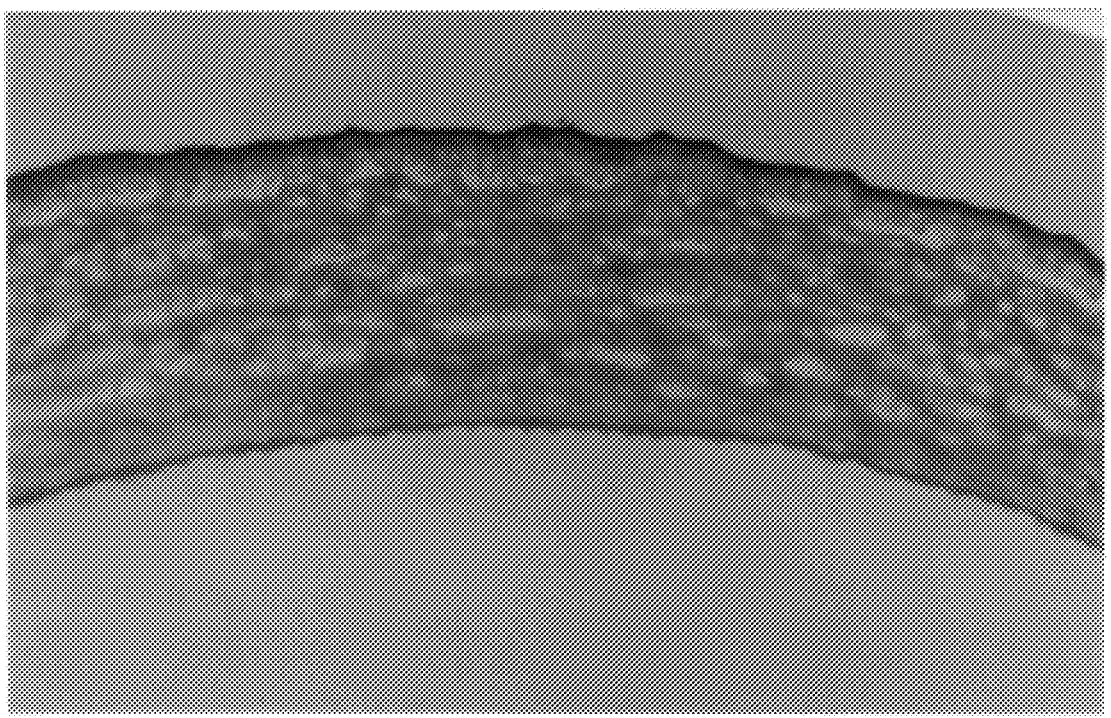
*FIG._2B*

OCULAR GENE THERAPY

FIELD OF THE INVENTION

The invention relates to methods of ocular gene therapy.

BACKGROUND OF THE INVENTION

Gene therapy treatments are rapidly becoming a reality, with several dozen gene therapy protocols approved by the National Institutes of Health, many of which being currently underway.

There are a number of ocular diseases and conditions which could be suitable for treatment with ocular gene therapy. These diseases fall into two categories, ocular disease caused by a specific genetic disorder, whether dominant or recessive, and diseases which have no currently known genetic basis but instead could be treated with the introduction of genes expressing proteins useful in the treatment of the condition.

In the first category, there are a number of diseases for which the underlying genetic defect is known. Autosomal retinitis pigmentosa, both dominant and recessive, may be caused by as many as 50 different mutations in the rhodopsin gene (Bok, Invest. Ophthalm. and Visual Sci. 34(3):473 (1993)). Autosomal dominant retinitis punctata albescens, butterfly-shaped pigment dystrophy of the fovea, and adult vitelliform macular dystrophy, have been correlated to a mutation in the peripherin/RDS gene (Kajiwara et al., Nature Genetics 3: 208 (1993); Nichols et al., Nature Genetics 3:202 (1993); Wells et al., Nature Genetics 3:213 (1993)). Norrie's disease (Berger et al., Nature Genetics 1:199 (1992)), blue cone monochromasy (Nathans et al., Science 245:831 (1989)), and choroideremia (Cremers et al., Nature 347:674 (1990); Merry et al., Proc. Natl. Acad. Sci. USA 89:2135 (1992)) have all been shown to be caused by genetic mutations. The gene for gyrate atrophy involves more than 60 different mutations in the mitochondrial enzyme ornithine aminotransferase (Bok, supra).

In addition to the diseases for which specific genetic mutations are known to cause the phenotype, there are a number of diseases for which the specific genetic component is unknown. These diseases may have a genetic basis or may be caused by other factors resulting in changes in protein expression. For example, age-related macular degeneration is a significant ocular disease among older patients. Retinoblastoma, anterior and posterior uveitis, retinovascular diseases, cataracts, inherited corneal defects such as corneal dystrophies, retinal detachment and degeneration and atrophy of the iris fall into this category, as do retinal diseases which are secondary to glaucoma and diabetes, such as diabetic retinopathy.

Finally, there are a number of conditions which are not genetically based but are still significant ocular diseases. For example, viral infections such as Herpes Simplex Virus (HSV) or cytomegalovirus (CMV) infections frequently cause significant symptoms, and may cause blindness. Retinal detachment, diabetic retinal disease, retinal vein thrombosis, retinal artery embolism, allergic conjunctivitis and other ocular allergic responses, dry eye, lysosomal storage diseases, glycogen storage diseases, disorders of collagen, disorders of glycosaminoglycans and proteoglycans, sphinogolipodoses, mucolipidoses, disorders of amino aicd metabolism, dysthyroid eye diseases, antierior and posterior corneal dystrophies, retinal photoreceptor disorders, corneal ulceration and other ocular wounds such as those following surgery are also significant conditions which do not have a known genetic component.

Recent work has shown that the retinal degeneration phenotype of the rd mouse, which has served as a model for the study of human retinitis pigmentosa for over 30 years, may be rescued by the expression of a bovine cGMP phosphodiesterase β-subunit in transgenic rd mice (Lem et al., Proc. Natl. Acad. Sci. USA. 15:442 (1992)). Similarly, the retinal degeneration slow (rds) phenotype of the rds mouse may also be corrected by the creation of transgenic mice expressing the wild-type rds gene product, a 39 kD membrane-associated glycoprotein (Travis et al., Neuron, 9:113 (1992)). However, as pointed out by several commentators, transgenic techniques are not directly applicable to human therapy, due to the uncertainties of transgene insertion (Zack, Arch. Ophthalmol. 111:1477 (1993), Bok, supra).

Additionally, in vitro gene transfer using a retroviral vector has been done on cells deficient in β-glucoronidase, an enzyme deficiency which is inherited in an autosomal recessive manner. After transformation with the gene coding for the enzyme, the β-glucuronidase deficient cells exhibited normal enzyme activity (Stramm et al., Exp. Eye Res 50:521–532 (1990)).

Recently, two in vivo protocols using adenoviral vectors have been reported. Bennett et al., Investigative Ophthalmology and Visual Science, 1994, 35(5):2535; Li et al., Investigative Ophthalmology and Visual Science, 1994, 35(5):2543.

Therefore, there is a need for in vivo and in situ ocular gene therapy. Accordingly, it is an object of the invention to provide methods for the generation of genetically-engineered ocular cells, and specifically, methods for the generation of genetically-engineered in situ ocular cells.

SUMMARY OF THE INVENTION

The present invention is based on the determination that in situ ocular cells may be genetically-engineered to produce exogeneous proteins.

In one aspect, the invention provides methods for generating genetically-engineered ocular cells. The method comprises contacting an ocular cell with exogeneous nucleic acid under conditions which are permissive for the uptake of the exogeneous nucleic acid into the ocular cell.

In a further aspect, the invention provides methods for introducing exogeneous nucleic acids to an in situ ocular cell. The method comprises contacting the ocular cell with suitable exogeneous nucleic acid under conditions permissive for the uptake of the exogeneous nucleic acid into the ocular cell.

In one aspect, the invention provides a method for treating an ocular disease. The method comprises incorporating exogeneous nucleic acid into an in situ ocular cell, wherein the exogeneous nucleic acid encodes a protein associated with the ocular disease.

In an additional aspect, the invention provides methods for treating ocular disease. The method comprises incorporating exogeneous nucleic acid into an in situ ocular cell, wherein the exogeneous nucleic acid encodes a protein useful in the treatment of the ocular disease.

In a further aspect, the invention provides ocular cells containing exogeneous nucleic acid.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIGS. 1A and 1B depict the histochemical X-gal staining of frozen sections of corneal epithelium. The blue X-gal staining of FIG. 1A shows gene delivery of the β-galactosidase marker to the basal epithelial cells on the corneal surface, after debridement as outlined in Example 1. FIG. 1B is the control, showing the lack of staining. Both sections were counterstained with eosin.

FIGS. 2A and 2B depict the histochemical X-gal staining of frozen sections of corneal endothelium. The blue X-gal staining of FIG. 1A shows gene delivery of the β-galactosidase marker to the endothelial cells on the corneal surface. FIG. 2B is the control, showing the lack of staining. Both sections were counterstained with eosin.

DETAILED DESCRIPTION OF THE INVENTION

The invention is based on the discovery that exogenous nucleic acid may be introduced into ocular cells, and in particular in situ ocular cells. Thus, methods are provided for generating a genetically-engineered in situ ocular cell. The method comprises contacting an ocular cell with exogenous nucleic acid under conditions that allow the ocular cell to take up the exogenous nucleic acid into said ocular cell and express it.

By the term "in situ ocular cell" or grammatical equivalents herein is meant an ocular cell contained within the eye, i.e. in vivo. Ocular cells include cells of the lens, the cornea (both endothelial, stromal and epithelial corneal cells), the iris, the retina, choroid, sclera, ciliary body, vitrous body, ocular vasculature, canal of Schlemm, ocular muscle cells, optic nerve, and other ocular sensory, motor and autonomic nerves.

By the term "genetically-engineered" herein is meant a cell or tissue that has been subjected to recombinant DNA manipulations, such as the introduction of exogenous nucleic acid, resulting in a cell or tissue that is in a form not ordinarily found in nature. For example, the cell contains exogenous nucleic acid. Generally, the exogenous nucleic acid is made using recombinant DNA techniques. It is understood that once a genetically engineered cell or tissue is made, it may replicate non-recombinantly, i.e. using the in vivo cellular machinery of the host cell, but will still be considered genetically-engineered for the purposes of the invention.

By the term "nucleic acid" or grammatical equivalents herein is meant either DNA or RNA, or molecules which contain both ribo- and deoxyribonucleotides. The nucleic acids include genomic DNA, cDNA and oligonucleotides including sense and anti-sense nucleic acids. The nucleic acid may be double stranded, single stranded, or contain portions of both double stranded or single stranded sequence.

By the term "exogenous nucleic acid" or "foreign nucleic acid" or "recombinant nucleic acid" or grammatical equivalents herein is meant nucleic acid which encodes proteins not ordinarily made in appreciable or therapeutic amounts in ocular cells. Thus, exogenous nucleic acid includes nucleic acid which is not ordinarily found in the genome of the ocular cell, such as heterologous nucleic acid from other organisms. Exogenous nucleic acid also includes nucleic acid which is ordinarily found within the genome of the ocular cell, but is in a form which allows for the expression of proteins which are not ordinarily expressed in ocular cells in appreciable or therapeutic amounts. For example, while human neurotrophins such as nerve growth factor (NGF) and neurotrophin-3 (NT3) are encoded within the genome of human ocular cells, they are not ordinarily expressed in human ocular tissue in significant or therapeutic amounts. Thus, a human gene is exogenous to a human ocular cell if it contains a promoter or is in some form which allows for the increased expression of the protein within the ocular cell. Thus the genetically engineered ocular cell may contain extra copies of a gene ordinarily found within its genome. Alternatively, the exogenous nucleic acid may encode a variant or mutant form of a naturally-occurring protein.

It is understood that once an exogenous nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered "exogenous" or "recombinant" for the purposes of the invention.

In the preferred embodiment, the exogenous nucleic acid encodes a protein to be expressed. That is, it is the protein which is used to treat the ocular disease. In an alternative embodiment, the exogenous nucleic acid is an anti-sense nucleic acid, which will inhibit or modulate the expression of a protein. In this embodiment, the exogenous nucleic acid need not be expressed. Thus, for example, ocular tumor cells may express undesirable proteins, and the methods of the present invention allow for the addition of anti-sense nucleic acids to regulate the expression of the undesirable proteins. Similarly, the expression of mutant forms of a protein may cause ocular disease. It is possible to incorporate both anti-sense nucleic acid to reduce the level of expression of the mutant endogenous gene as well as nucleic acid encoding a correct copy of the gene.

In an additional embodiment, the exogenous nucleic acid may encode a regulatory protein such as a transcription or translation regulatory protein. In this embodiment, the protein itself may not directly affect the ocular disease, but instead may cause the increase or decrease in the expression of another protein which affects the ocular disease.

In one embodiment, the exogenous nucleic acid encodes a single protein. In alternative embodiments, the exogeneous nucleic acid encodes more than one protein. Thus, for example, several proteins which are useful to treat an ocular disorder may be desirable; alternatively, several ocular diseases may be treated at once using exogenous nucleic acid encoding several proteins.

Similarly, an "exogenous" or "recombinant protein" is a protein made using recombinant techniques, i.e. through the expression of an exogeneous or recombinant nucleic acid as described above. A recombinant protein is distinguished from naturally occurring protein by at least one or more characteristics. For example, the protein may be made at a significantly higher concentration than is ordinarily seen, through the use of a inducible promoter or high expression promoter, such that increased levels of the protein is made. Thus, for instance, an exogenous protein is one which is not ordinarily expressed in ocular tissue. Alternatively, the protein may be in a form not ordinarily found in nature, as in the addition of an epitope tag or amino acid substitutions, insertions and deletions.

In a preferred embodiment, the exogenous nucleic acid encodes a protein useful in the treatment of ocular diseases. By "ocular disease" herein is meant a disorder or pathological condition of the eye which is not normal to the animal in a healthy state.

In one embodiment, the ocular disease may be caused by a genetic defect. Examples of such ocular diseases for which a gene has been identified include, but are not limited to, autosomal retinitis pigmentosa, autosomal dominant retinitis punctata albescens, butterfly-shaped pigment dystrophy of the fovea, adult vitelliform macular dystrophy, Norrie's disease, blue cone monochromasy, choroideremia and gyrate atrophy. These may also be referred to as genetic ocular diseases.

In other embodiments, the ocular disease may not be caused by a specific known genotype (although they may be shown in the future to have a genetic component). These ocular diseases include, but are not limited to, age-related macular degeneration, retinoblastoma, anterior and posterior uveitis, retinovascular diseases, cataracts, inherited corneal defects such as corneal dystrophies, retinal detachment and degeneration and atrophy of the iris, and retinal diseases which are secondary to glaucoma and diabetes, such as diabetic retinopathy.

In addition, the term ocular disease includes conditions which are not genetically based but still cause ocular disorders or disfunctions. These include, but are not limited to, viral infections such as Herpes Simplex Virus or cytomegalovirus (CMV) infections, allergic conjunctivitis and other ocular allergic responses, dry eye, lysosomal storage diseases, glycogen storage diseases, disorders of collagen, disorders of glycosaminoglycans and proteoglycans, sphinogolipodoses, mucolipidoses, disorders of amino aicd metabolism, dysthyroid eye diseases, anterior and posterior corneal dystrophies, retinal photoreceptor disorders, corneal ulceration and other ocular wounds such as those following surgery.

By the term "conditions permissive for the uptake of exogenous nucleic acid" herein is meant experimental conditions which allow the in situ ocular cell to take up, and be transformed with, the exogenous nucleic acid.

The permissive conditions will depend on the form of the exogenous nucleic acid. Thus, for example, when the exogenous nucleic acid is in the form of an adenoviral, retroviral, or adenoassociated viral vector, the permissive conditions are those which allow viral infection of the cell. Similarly, when the exogenous nucleic acid is in the form of a plasmid, the permissive conditions allow the plasmid to enter the cell. Thus, the form of the exogenous nucleic acid and the conditions which are permissive for its uptake are correlated. These conditions are generally well known in the art.

In a preferred embodiment, the nucleic acid encodes a protein which is expressed. In some embodiments, the expression of the exogenous nucleic acid is transient; that is, the exogenous protein is expressed for a limited time. In other embodiments, the expression is permanent. Thus for example, transient expression systems may be used when therapeutic proteins are to be delivered for a short period; for example, certain exogenous proteins are desirable after ocular surgery or wounding. Alternatively, for on-going or congenital conditions such as retinitis pigmentosa or glaucoma, permanent expression may be desired.

In some embodiments, the exogenous nucleic acid is incorporated into the genome of the target cell; for example, retroviral vectors described below integrate into the genome of the host cell. Generally this is done when longer or permanent expression is desired. In other embodiments, the exogenous nucleic acid does not incorporate into the genome of the target cell but rather exists autonomously in the cell; for example, many such plasmids are known. This embodiment may be preferable when transient expression is desired.

Permissive conditions depend on the expression vector to be used, the amount of expression desired and the target cell. Generally, conditions which allow in vitro uptake of exogenous cells work for in vivo ocular cells. In some cases, the physical structural characteristics of the eye are taken into consideration.

For example, when the target cells are corneal epithelial cells, permissive conditions may include the debridement, or scraping of the corneal epithelium, in order to denude the corneal surface down to a basal layer of epithelium. The exogenous nucleic acid is then added, in a variety of ways as described below.

Permissive conditions are analyzed using well-known techniques in the art. For example, the expression of exogenous nucleic acid may be assayed by detecting the presence of mRNA, using northern hybridization, or protein, using antibodies or biological function assays.

Specific conditions for the uptake of exogenous nucleic acid are well known in the art. They include, but are not limited to, retroviral infection, adenoviral infection, transformation with plasmids, transformation with liposomes containing exogenous nucleic acid, biolistic nucleic acid delivery (i.e. loading the nucleic acid onto gold or other metal particles and shooting or injecting into the cells), adenoassociated virus infection and Epstein-Barr virus infection. These may all be considered "expression vectors" for the purposes of the invention.

The expression vectors may be either extrachromosomal vectors or vectors which integrate into a host genome as outlined above. Generally, these expression vectors include transcriptional and translational regulatory nucleic acid operably linked to the exogenous nucleic acid. "Operably linked" in this context means that the transcriptional and translational regulatory DNA is positioned relative to the coding sequence of the exogenous protein in such a manner that transcription is initiated. Generally, this will mean that the promoter and transcriptional initiation or start sequences are positioned 5' to the exogenous protein coding region. The transcriptional and translational regulatory nucleic acid will generally be appropriate to the ocular host cell used to express the exogenous protein; for example, transcriptional and translational regulatory nucleic acid sequences from mammalian cells, and particularly humans, are preferably used to express the exogenous protein in mammals and humans. Preferred are ocular cell transcriptional and translational regulatory sequences. Numerous types of appropriate expression vectors, and suitable regulatory sequences are known in the art.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

Suitable retroviral vectors include LNL6, LXSN, and LNCX.

Suitable adenoviral vectors include modifications of human adenoviruses such as Ad2 or Ad5, wherein genetic elements necessary for the virus to replicate in vivo have been removed; e.g. the E1 region, and an expression cassette coding for the exogenous gene of interest inserted into the adenoviral genome (for example $Ad_{GV}CFTR_{10}$).

By "protein associated with an ocular disease" herein is meant a protein encoded by a gene identified as the origin of a genetic ocular disease. Thus, for those ocular diseases for which the genetic component has been identified, such as retinitis pigmentosa, the associated protein is rhodopsin. Thus, the absence or presence of the associated protein is either the result or cause of the genetic ocular disease.

By "protein useful in the treatment of an ocular disease" herein is meant a protein which is effective to alleviate the symptoms of the ocular disease. The ocular disease may be genetic, or may not have a genetic component. Thus, for example, ocular wounds, allergies, viral infections, ulcerations, etc. may be treated with useful proteins. For instance, gD is a protein useful in the treatment of herpes simplex virus infections, transforming growth factor β (TGFB) in corneal epithelial wounds; anti-IgE antibody for ocular allergy, and brain derived neutrophic factor (BDNF) for retinal degeneration. Neural growth factor (NGF) and neurotrophin 5 (NT5), as well as fusions and/or mutants of these, may be used for retinal degeneration or to delay or prevent damage after retinovascular disease, or retinal detachment or glaucoma. These neurotrophic factors may also be used to treat optic nerve compression, trauma or demyelination. Immunosuppressive proteins may be used to treat graft rejection after corneal transplantation. Vascular endothelial cell growth factor (VEGF) antagonists, such as antibodies or small molecules, may be used to treat neovascular disorders of the retina and vitreous. Basic fibroblast growth factor has been shown to prolong photoreceptor life in rats (Faktorovich et al., Nature 347:83–86 (1990).

In one embodiment, the exogenous nucleic acid is delivered to corneal epithelial cells. Corneal epithelial cells are subject to injury, allergic reactions and infections, among others. Thus proteins which are useful in the treatment of these conditions, and others, may be delivered via the present invention.

In another embodiment, the exogenous nucleic acid is delivered to corneal endothelial cells. This is particularly significant since dysfunction of the corneal endothelial cells causes blindness. This layer is often damaged during cataract extraction, which is currently the most common surgical operation in the U.S. In addition, since the corneal endothelium cannot regenerate, since cell division does not occur, the expression of proteins which cause division or regeneration of corneal endothelial cells could be a significant treatment of corneal endothelial damage.

In another embodiment, exogenous nucleic acid is introduced into the cells of the trabecular meshwork, beneath the periphery of the cornea. The trabecular meshwork is the outflow tract from the anterior chamber of the eye, which allows aqueous humor (the fluid contained within the eye) to drain from the eye. This is significant since glaucoma is a common cause of visual loss in the U.S., and is a result of increased intraocular pressure. Therefore, the methods of the present invention may be useful to regulate the outflow of aqueous humor and treat or cure glaucoma.

In one embodiment, the exogenous nucleic acid is introduced to cells of the choroid layer of the eye. The choroid layer of the eye is part of the blood supply to the retina, and thus may supply proteins to the retina. For example, BDNF (brain-derived neurotrophic factor) may be delivered in this manner to treat retinal degeneration.

In alternative embodiments, the exogenous nucleic acid is introduced to cells of the retina, sclera or ciliary body. This last may be done, for example, for controlling production of aqueous fluid in the treatment or prevention of glaucoma.

Similarly, additional embodiments utilize the introduction of exogenous nucleic acid to the cells of the retinal or ocular vasculature, cells of the vitreous body or cells of the lens, for example the lens epithelium.

"Animal" as used herein includes both humans and other animals and organisms. Thus the methods are applicable to both human therapy and veterinary applications. For example, the veterinary applications include, but are not limited to, canine, bovine, feline, porcine, equine, and ovine animals, as well as other domesticated animals including reptiles, birds, rabbits, and rodents such as rats, mice, guinea pigs and hamsters. Valuable non-domesticated animals, such as zoo animals, may also be treated. In the preferred embodiment the animal is a mammal, and in the most preferred embodiment the animal is human.

In addition, the methods outlined in the present invention are useful in the creation of ocular disease animal models. That is, mutated copies of genes may be introduced into animals to create models for drug screening and therapy. For example, genes in which mutations are known to cause ocular disease, or to play a role in ocular disorders, may be introduced into animals such as rodents and rabbits, resulting in ocular disease. For example, granulocyte macrophage colony stimulating factor (GM-CSF) may be expressed in intraocular macrophages to create a retinal degeneration model. Similarly, S-antigen may be expressed in the eye to generate a model of uveitis.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. The references cited herein are expressly incorporated by reference.

EXAMPLES

Example 1

Delivery of Exogenous Nucleic Acid to Corneal Epithelial Cells

A β-galactosidase-expressing recombinant adenoviral vector was constructed by first building a shuttle plasmid, in which the CMV/β galactosidase expression cassette was flanked by adenovirus DNA sequences, such that when cotransfected with the adenoviral deletion mutant DNA dl324 into 293 cells, a homologous recombination event placed the β-galactosidase expression cassette into the E1 region of the virus. The resulting E1-deficient recombinant virus was thus replication incompetent in all cells but 293 cells, and expressed the E. coli β-galactosidase gene. This gene product may be assayed for its enzyme function, or assayed histochemically by exposing the enzyme to a substrate, X-gal, resulting in a characteristic blue stain in the cells that are expressing the marker gene.

The recombinant, replication-incompetent viral vectors were produced in 293 cells, a human fetal kidney cell line, which expressed the E1 protein in trans.

20$\mu$ of the 1×10$^9$ pfu/ml viral vector preparation was applied topically in a balanced, buffered salt solution (10 mM Tris, pH 7.5, 1 mM $MgCl_2$, 10% glycerol) to the intact corneal epithelium of anesthetized Sprague Dawley rats. The viral solution was left in place for 30 minutes, and then the solution was removed and the eye surface coated with a protective aqueous ointment (Rugby Artificial Tears: white petrolatum, mineral oil and anhydrous lanolin). The animals were allowed to recover, and were then sacrificed 24 hours later. The eyes were frozen in Tissue Tek, histologic sections were cut at 7 μm thickness, and the sections stained histochemically to detect β-galactosidase expression. Control animals received the vehicle alone topically, and their eyes were processed in the same way. Neither the test animals, nor the control animals showed β-galactosidase expression in their corneal epithelial cells.

The corneal epithelium is a stratified, squamous epithelium. The outermost cells are flattened and regularly physiologically slough from the surface, while being renewed from the less-well-differentiated cells below. We reasoned that perhaps because of the structure of the corneal epithelium, the outer epithelial cells, which were the cells to which we might have achieved gene transfer, had sloughed off by the time we examined the eyes 24 hours ofter gene delivery.

We reasoned that surgically removing the outermost layers of the cornea epithelium, prior to topical gene delivery, would allow gene delivery to these deeper, more long-lived cells, which might then express the delivered gene and survive in vivo for a prolonged period. Such a surgical removal of superficial epithelial cells is called 'debridement', and is done in conjunction with treatment for a number of cornea epithelial disease states, including corneal ulceration.

We therefore did an experiment to gauge the rate of recovery of the corneal epithelium in rats following superficial epithelial debridement. The cornea epithelium of anesthetized rats were scraped with a scalpel blade in a reproducible fashion. The eyes were then examined histologically at time intervals of 5 minutes, 1 hour, 16 hours and 2 days, to look for epithelial repair. We found that by 16 hours after the surgery, it was impossible to see a difference between an unoperated eye and an eye that had the superficial corneal epithellum removed.

Therefore, in a second series of experiments, we debrided the superficial corneal epithelium using the scraping procedure outlined above, and immediately applied 20 μl of a $1 \times 10^9$ pfu/ml solution of recombinant adenovirus to the corneal surface for 30 minutes. Animals were then sacrificed 24 hours later as before. As shown in FIGS. 1A and 1B, histochemical staining of sections of these eyes revealed extensive β-galactosidase marker gene expression in the corneal epithelial cells of the animals given topical adenoviral vector, while there was no expression in the control animals.

Example 2

Delivery of Exogenous Nucleic Acid to Corneal Endothelial Cells

20 μl of aqueous humor from the anterior chamber of anesthetized rats was removed using a 30 g needle and a Hamilton syringe. This fluid was replaced with 20 μl of a $1 \times 10^9$ pfu/ml solution of the replication-incompetent recombinant adenoviral vector described above which delivered a β-galactosidase marker gene. Control rats were treated in the same way, but received vehicle alone. 24 hours later the animals were sacrificed, and the eyes were mounted in Tissue Tek, frozen, sectioned and stained for β-galactosidase protein. As shown in FIGS. 2A and 2B, there was clear positive staining of the majority of cells lining the posterior surface of the cornea (the corneal endothelial cells) in the animals that received the viral vector, but no staining in the animals that received vehicle alone. Furthermore, there was also staining of the cells of the ciliary body epithelium in animals that received vector.

Example 3

Delivery of Exogenous Nucleic Acid to Choroid Ocular Cells

5 μl of a $1 \times 10^9$ pfu/ml solution of a β-galactosidase expressing recombinant adenoviral vector was injected into the vitreous humor (posterior segment) of the eye in anesthetized rats. Control rats were treated in the same way, but received vehicle alone. 24 hours later the animals were sacrificed, and the eyes were mounted in Tissue Tek, frozen, sectioned and stained for β-galactosidase protein. There was clear positive staining of some of the cells of the choroid, which is the vascular coat surrounding the posterior part of the eye. There was no such staining in animals that received vehicle alone.

I claim:

1. A method for generating a genetically-engineered in situ ocular cell, said method comprising contacting an ocular cell with exogenous nucleic acid under conditions permissive for the uptake of said exogenous nucleic acid into said ocular cell for expression therein.

2. A method according to claim 1 wherein said exogenous nucleic acid is in the form of a retrovirus.

3. A method according to claim 1 wherein said exogenous nucleic acid is in the form of an adenovirus.

4. A method according to claim 1 wherein said exogenous nucleic acid is in the form of a plasmid.

5. A method according to claim 1 wherein said exogenous nucleic acid is in the form of an adenoassociated virus.

* * * * *